United States Patent
Brunacci et al.

(10) Patent No.: US 6,519,536 B1
(45) Date of Patent: Feb. 11, 2003

(54) METHOD FOR DETERMINING THE BEHAVIOUR OF A VISCOELASTIC MATERIAL

(75) Inventors: Antonio Brunacci, Luxembourg (LU); Marco Nahmias Nanni, Milan (IT); Antonio Serra, Genoa (IT)

(73) Assignee: Pirelli Pneumatici S.p.A., Milan (IT)

( * ) Notice: Subject to any disclaimer, the term of this patent is extended or adjusted under 35 U.S.C. 154(b) by 0 days.

(21) Appl. No.: 09/536,394

(22) Filed: Mar. 28, 2000

Related U.S. Application Data

(60) Provisional application No. 60/126,721, filed on Mar. 29, 1999.

(30) Foreign Application Priority Data

Mar. 29, 1999 (EP) ............................................. 99200987

(51) Int. Cl.$^7$ ............................................. G06F 19/00
(52) U.S. Cl. ............................. 702/50; 702/41; 702/43; 703/2; 703/9
(58) Field of Search ........................... 703/2, 9; 702/42, 702/43, 50; 73/789

(56) References Cited

U.S. PATENT DOCUMENTS

| | | | |
|---|---|---|---|
| 4,667,519 A | 5/1987 | Burg et al. ..................... 73/815 |
| 5,452,614 A | 9/1995 | Kato et al. ..................... 73/789 |
| 5,675,253 A | * 10/1997 | Smith et al. ................. 324/306 |
| 5,784,283 A | 7/1998 | Rimondi et al. ............. 700/198 |
| 6,038,389 A | * 3/2000 | Rahon et al. ................. 703/10 |

FOREIGN PATENT DOCUMENTS

| | | |
|---|---|---|
| EP | 0 367 218 | 5/1990 |
| EP | 0 466 060 | 1/1992 |
| EP | 0 545 728 | 6/1993 |
| WO | 93 09419 | 5/1993 |

OTHER PUBLICATIONS

Sousa et al.; "Dynamic Properties of Asphalt Concrete", Journal of Testing and Evaluation, vol. 16, No. 4, pp. 350–363, (1988).

* cited by examiner

*Primary Examiner*—John S. Hilten
*Assistant Examiner*—Stephen J. Cherry
(74) *Attorney, Agent, or Firm*—Finnegan, Henderson, Farabow, Garrett & Dunner, L.L.P.

(57) ABSTRACT

A method for determining behavior of a viscoelastic material at a first temperature includes performing five or more measurements of a dynamic parameter as a function of deformation at each of at least a second, third, and fourth temperature. Eleven or more data points are chosen from the measurements. Each data point comprises a value of the dynamic parameter, an associated deformation, and an associated temperature. Values of the eleven parameters are determined by inserting at least eleven of the data points into a first equation. The first temperature and the values of the eleven parameters are inserted into the first equation. The dynamic parameter is approximated as a function of the deformation at the first temperature using the first equation. A related apparatus is also disclosed.

18 Claims, 5 Drawing Sheets

METHOD FOR DETERMINING THE BEHAVIOUR OF A VISCOELASTIC MATERIAL

CROSS-REFERENCE TO RELATED APPLICATIONS

Applicants claim the right of priority under 35 U.S.C. § 119(a)–(d) based on patent application Ser. No. 99200987.8, filed Mar. 29, 1999, in the European Patent Office; additionally, Applicants claim the benefit under 35 U.S.C. § 119(e) based on prior-filed, copending U.S. Provisional Application No. 60/126,721, filed Mar. 29, 1999, in the U.S. Patent and Trademark Office; the contents of all of which are relied upon and incorporated herein by reference.

BACKGROUND OF THE INVENTION

1. Field of the Invention

The present invention relates to a method for determining the behaviour of a viscoelastic material.

It also relates to a method for improving the storage of experimental curves, a method for determining at least one viscoelastic material having predetermined characteristics and apparatus useful for this purpose.

2. Description of the Related Art

Among the properties of viscoelastic materials, those which are mainly associated with their use are the dynamic properties, or the responses to the application of deformations.

At present, in order to be able to select, at the time of use, the material which best satisfies the final dynamic requirements of a desired product, it is necessary to know the dynamic properties of a large number of materials and, therefore, to have first carried out numerous experimental measurements in order to characterize them.

These dynamic properties, however, depend on the temperature and, in the case of some materials, such as for example polymers containing reinforcing fillers or asphalts, also on the deformation applied. Consequently, the characterization of each material requires the acquisition of a large number of experimental values according to variation in the temperature and the deformation applied.

For example, in order to determine the dynamic properties of these materials, generally experimental measurements of the force following deformation cycles in a predetermined temperature range are performed.

Moreover, the storage of the abovementioned data requires a large amount of space or memory depending on whether it is stored on a paper medium or electronic medium. In the case of storage on a paper medium, moreover, a very long time is needed in order to check whether, with the stored experimental data, it is possible to identify a product having the required characteristics, at a certain temperature.

Another drawback inherent in the known methods is that it is possible to identify the product having the required characteristics only if experimental measurements have been performed at the temperature concerned at the moment when said identification is performed.

SUMMARY OF THE INVENTION

The inventors of the present invention, therefore, have considered the problem of simplifying the characterization, storage and selection processes which are currently used.

More precisely, considering the experimental curves of a dynamic parameter P as a function of a deformation q applied to a generic test piece of viscoelastic material at a temperature T, the inventors of the present invention have surprisingly discovered that these experimental curves are referable to a summation of exponentials of the type:

$$P(q, T) = a*T^2 + b*T + c + \sum_{i=1}^{\infty} (d_i*T^2 + e_i*T + f_i)*e^{-\frac{q}{q_i}} \quad (I)$$

where q is the deformation expressed in %;

T is the temperature expressed in Kelvin;

P(q,T) is a dynamic parameter preferably selected from the group comprising the elastic modulus, the viscous modulus, the complex modulus and the loss factor;

a, b, c are characteristic constants which depend on the type of viscoelastic material and the type of dynamic parameter considered;

$d_i$, $e_i$, $f_i$ are characteristic constants which depend on the effect of the temperature on the dynamic parameter P and on the ith characteristic deformation;

$q_i$ is the characteristic deformation at the ith exponential.

The inventors, moreover, have realized that, in order to obtain good approximation of said experimental curves, it is sufficient to perform the abovementioned summation (I) as far as the second term. In such a case, therefore, there are only 11 parameters to be determined for each dynamic parameter P of each viscoelastic material, namely, a, b, c, $q_1$, $q_2$, $d_1$, $e_1$, $f_1$, $d_2$, $e_2$ and $f_2$.

In the case where, on the other hand, it is desired to obtain a greater accuracy, it is sufficient to perform the abovementioned summation (I) as far as the higher term, which ensures the desired accuracy. Obviously, in this case, the number of parameters which must be determined will gradually increase.

Therefore, even though the description which follows is mainly based on carrying out the summation as far as the second term, the person skilled in the art will not have any difficulty in determining the required parameters and in carrying out the abovementioned summation (I) up to any term higher than the second term which ensures the desired accuracy.

For example, in the case of the experimental curves for the elastic modulus G', measured at different temperature values T, as a function of a torsion γ applied to a cylindrical test piece consisting of a compound for a tyre containing a reinforcing filler, the inventors have found that these experimental curves are referable, according to the present invention, to the relation:

$$G'(\gamma, T) = a*T^2 + b*T + c + \\ (d_1*T^2 + e_1*T + f_1)*e^{-\frac{\gamma}{\gamma_1}} + (d_2*T^2 + e_2*T + f_2)*e^{-\frac{\gamma}{\gamma_2}}$$

Furthermore, investigating also the experimental curves of the complex modulus G*, viscous modulus G"

(where $|G^*|=\sqrt{(G')^2+(G'')^2}$)

and the loss factor tan δ (where tan δ=G"/G') as a function of the torsion γ, applied to the test piece, and of the temperature T, the inventors have surprisingly found that they may also be represented by the abovementioned summation of exponentials and that in order to obtain a good approximation, for each of the abovementioned experimental curves, 11 parameters are sufficient, as illustrated above.

Finally, the inventors have even more surprisingly found that the values of the parameters a, b, c, $q_1$, $q_2$, $d_1$, $e_1$, $f_1$, $d_2$, $e_2$ and $f_2$, which have been determined on the basis of at least 5 experimental measurements, carried out at each of at least three temperatures $T_x$, $T_y$, $T_z$, of a dynamic parameter P of a viscoelastic material as a function of a deformation q, may be used to determine the progression of said dynamic parameter P as a function of said deformation q also at a temperature $T_w$ different from $T_x$, $T_y$ and $T_z$. Thus, with this method the progression of said dynamic parameter P is determined as a function of said deformation q at a temperature $T_w$ for which no experimental determination was performed.

According to a first aspect thereof, the present invention therefore relates to a method for determining the behaviour of a viscoelastic material at a temperature $T_w$ characterized in that a) N experimental measurements, where N≧5, of a dynamic parameter P as a function of a deformation q at each of at least three temperatures $T_x$, $T_y$, $T_z$ different from $T_w$ are performed;

b) for each of said at least three temperatures $T_x$, $T_y$, $T_z$, the experimental curve which passes through all the points which represent the N values determined experimentally in said step a) is plotted;

c) at least 11 values of said dynamic parameter P and of the associated deformation q distributed along the experimental curves plotted in said step b) at said at least three temperatures $T_x$, $T_y$, $T_z$ are chosen;

d) said at least 11 values are inserted in the relation (A):

$$P(q, T) = a*T^2 + b*T + c + (d_1*T^2 + e_1*T + f_1)*e^{-\frac{q}{q_1}} + (d_2*T^2 + e_2*T + f_2)*e^{-\frac{q}{q_2}}$$

so as to determine, for subsequent approximations, values of parameters a, b, c, $q_1$, $q_2$, $d_1$, $e_1$, $f_1$, $d_2$, $e_2$, $f_2$ of said relation (A) which generate the curves which best approximates said experimental curves plotted in step b); and e) the temperature $T_w$ and the values of said parameters a, b, c, $q_1$, $q_2$, $d_1$, $e_1$, $f_1$, $d_2$, $e_2$, $f_2$ obtained in the previous step d) are inserted in said relation (A) in order to determine the progression of said dynamic parameter P as a function of the deformation q at the temperature $T_w$.

More particularly, during said determination for subsequent approximations of step d)

d1) an arbitrary value for each of said parameters a, b, c, $q_1$, $q_2$, $d_1$, $e_1$, $f_1$, $d_2$, $e_2$, $f_2$ is inserted in said relation (A);

d2) by means of said relation (A) at least 11 values of said parameter P are determined as a function of the values of said deformation q indicated in the abovementioned step c);

d3) the differences between the values, thus determined, of said parameter P and the corresponding values of P indicated in the abovementioned step c) are calculated;

d4) the squares of the abovementioned differences are added together;

d5) the value thus obtained of the sum of the squares of the abovementioned differences is stored;

d6) on the basis of the value obtained for said sum, another value is assigned to each of the parameters a, b, c, $q_1$, $q_2$, $d_1$, $e_1$, $f_1$, $d_2$, $e_2$, $f_2$ so as to reduce this sum of the squares of the differences;

d7) the steps from d2) to d6) are repeated until the value of the sum of the squares of the differences is minimized;

d8) the values of said parameters a, b, c, $q_1$, $q_2$, $d_1$, $e_1$, $f_1$, $d_2$, $e_2$, $f_2$ which minimized the value of said sum are stored.

These latter values, which are inserted in the abovementioned relation (A), generate the curves which best approximate the experimental curves plotted in the abovementioned step b).

Preferably, at least some of said at least 11 values of the deformation q, used in step d2) to determine P by means of the relation (A), are selected from among those used during the preceding step a). More preferably, all said at least 11 values of the deformation q used in step d2) are chosen from among the values of the deformation q used in said step a).

Preferably, in the abovementioned step c), at least two values of said dynamic parameter P and the associated deformation q for each of said experimental curves are chosen. More preferably, in the abovementioned step c), at least three values of said dynamic parameter P and the associated deformation q for each of said experimental curves are chosen.

Typically, said dynamic parameter P is selected from the group comprising the elastic modulus P', the viscous modulus P", the complex modulus P* and the loss factor tanδ of said viscoelastic material. Moreover, said deformation q is selected from the group comprising a torsion γ, a cutting force τ, a tensioning force and a flexing force.

Advantageously, said at least three temperatures $T_x$, $T_y$, $T_z$ are selected in a range of temperatures laying between −55° C. and 90° C.

When it is required to obtain greater accuracy, the additional parameters required are determined and in place of the abovementioned relation (A) the following summation (I) is performed:

$$P(q, T) = a*T^2 + b*T + c + \sum_{i=1}^{\infty} (d_i*T^2 + e_i*T + f_i)*e^{-\frac{q}{q_i}} \quad (I)$$

where q is the deformation expressed in %;

T is the temperature expressed in Kelvin;

a, b, c are characteristic constants which depend on the type of viscoelastic material and on the type of dynamic parameter considered;

$d_i$, $e_i$, $f_i$ are characteristic constants which depend on the effect of the temperature on the dynamic parameter P and on the ith characteristic deformation;

$q_i$ is the characteristic deformation at the ith exponential.

According to a second aspect thereof, the present invention relates to a method for improving the storage of at least three experimental curves, each obtained from at least N measured experimental values, where N is equal to at least 5, of a dynamic parameter P of a viscoelastic material as a function of a deformation q at one of at least 3 predetermined temperatures $T_x$, $T_y$, $T_z$, said method being characterized in that it comprises the steps of:

a) choosing at least 11 values of said dynamic parameter P and the associated deformation q distributed along said at least 3 experimental curves obtained at said at least 3 temperatures $T_x$, $T_y$, $T_z$;

b) inserting said at least 11 values in the relation (A):

$$P(q, T) = a*T^2 + b*T + c + (d_1*T^2 + e_1*T + f_1)*e^{-\frac{q}{q_1}} + (d_2*T^2 + e_2*T + f_2)*e^{-\frac{q}{q_2}}$$

so as to determine, for subsequent approximations, values for the parameters a, b, c, $q_1$, $q_2$, $d_1$, $e_1$, $f_1$, $d_2$, $e_2$, $f_2$ of said relation (A) which generate the curves which best approximate said at least 3 experimental curves;

c) storing the values of said parameters a, b, c, $q_1$, $q_2$, $d_1$, $e_1$, $f_1$, $d_2$, $e_2$, $f_2$ thus obtained.

As regards the characteristics of said determination for subsequent approximations, said dynamic parameter P, said deformation q and said temperatures $T_x$, $T_y$, $T_z$, reference should be made to that already stated above in connection with the method for determining the behaviour of a viscoelastic material at a temperature $T_w$.

According to a third aspect thereof, the present invention relates to a method for defining, from among a plurality of viscoelastic materials, at least one viscoelastic material having a dynamic parameter P which, at a preselected temperature $T_w$ and deformation $q_W$, has a predetermined value $P_W$, said method being characterized in that it comprises the steps of a) determining, for each of said plurality of viscoelastic materials, the value which said dynamic parameter P assumes at said temperature $T_w$ for said deformation $q_w$ by means of the relation (A.1)

$$P(q_w, T_w) = a*T_w^2 + b*T_w + c + (d_1*T_w^2 + e_1*T_w + f_1)*e^{-\frac{q_w}{q_1}} + (d_2*T_w^2 + e_2*T_w + f_2)*e^{-\frac{q_w}{q_2}}$$

where, for each of said plurality of viscoelastic materials, the values of the parameters a, b, c, $q_1$, $q_2$, $d_1$, $e_1$, $f_1$, $d_2$, $e_2$, $f_2$ have already been determined beforehand;

b) comparing each of the values of said parameter P thus determined with said value $P_w$; and c) defining the viscoelastic materials for which, at the temperature $T_w$ and for the deformation $q_w$, said dynamic parameter P satisfies said predetermined value $P_w$.

Preferably, said parameters a, b, c, $q_1$, $q_2$, $d_1$, $e_1$, $f_1$, $d_2$, $e_2$, $f_2$ of the abovementioned step a) were determined in a manner similar to that already described further above in connection with the first and the second aspect of the present invention.

Moreover, as regards the characteristics of said dynamic parameter P, said deformation $q_w$ and said temperature $T_w$, reference should be made to that stated further above in connection with P, q, $T_x$, $T_y$ and $T_z$.

According to a fourth aspect thereof, the present invention relates to an apparatus for processing data relating to a viscoelastic material having a predetermined dynamic parameter P, said apparatus comprising a) an input for entering N experimentally determined values, where N≧5, of said dynamic parameter P as a function of a deformation q at each of at least three temperatures $T_x$, $T_y$, $T_z$;

b) a processing unit connected to said input, said processing unit being capable of b1) plotting, for each of said at least three temperatures $T_x$, $T_y$, $T_z$, the experimental curve which passes through all the points which represent said N experimental values entered via said input;

b2) choosing at least 11 values of said dynamic parameter P and the associated deformation q distributed along the experimental curves plotted in step b1) at said at least three temperatures $T_x$, $T_y$, $T_z$, and b3) inserting said at least 11 values in the relation (A)

$$P(q, T) = a*T^2 + b*T + c + (d_1*T^2 + e_1*T + f_1)*e^{-\frac{q}{q_1}} + (d_2*T^2 + e_2*T + f_2)*e^{-\frac{q}{q_2}}$$

so as to determine, for subsequent approximations, values for the parameters a, b, c, $q_1$, $q_2$, $d_1$, $e_1$, $f_1$, $d_2$, $e_2$, $f_2$ of said relation (A) which generate the curves which best approximate said experimental curves plotted in step b1);

c) a memory for storing the values of the parameters a, b, c, $q_1$, $q_2$, $d_1$, $e_1$, $f_1$, $d_2$, $e_2$, $f_2$ thus determined.

Advantageously, via said input a predetermined temperature $T_w$ different from said at least three temperatures $T_x$, $T_y$, $T_z$ is also entered; and said processing unit is also capable of determining, by means of said relation (A), in which the values of said parameters a, b, c, $q_1$, $q_2$, $d_1$, $e_1$, $f_1$, $d_2$, $e_2$, $f_2$ stored in said memory are inserted, the progression of said dynamic parameter P as a function of said deformation q at said temperature $T_w$.

Preferably, said apparatus also comprises an output for providing said progression of said dynamic parameter P as a function of the deformation q at the temperature $T_w$.

As regards the characteristics of said determination for subsequent approximations, said dynamic parameter P, said deformation and said temperatures $T_x$, $T_y$, $T_z$ and $T_w$, reference should be made to that already stated further above.

According to a fifth aspect thereof, the present invention relates to an apparatus for processing data relating to a plurality of viscoelastic materials having a dynamic parameter P, said apparatus comprising an input for entering a value $P_w$ which represents a reference value for said dynamic parameter P at a preselected temperature $T_w$ for a preselected deformation $q_w$;

a processing unit capable of i. determining, for each of said plurality of viscoelastic materials, the value which the associated dynamic parameter P assumes at said temperature $T_w$ and at said deformation $q_w$ by means of the relation (A.1)

$$P(q_w, T_w) = a*T_w^2 + b*T_w + c + (d_1*T_w^2 + e_1*T_w + f_1)*e^{-\frac{q_w}{q_1}} + (d_2*T_w^2 + e_2*T_w + f_2)*e^{-\frac{q_w}{q_2}}$$

where, for each of said plurality of viscoelastic materials, the values of the parameters a, b, c, $q_1$, $q_2$, $d_1$, $e_1$, $f_1$, $d_2$, $e_2$, $f_2$ have already been determined beforehand; and ii. comparing the value of said parameter P thus determined with said value $P_w$; and an output for providing, from amongst said plurality of viscoelastic materials, the viscoelastic materials for which, at the temperature $T_w$ and at the deformation $q_w$, said dynamic parameter P satisfies said value $P_w$.

According to a first embodiment, said apparatus also comprises a memory in which said values of said parameters a, b, c, $q_1$, $q_2$, $d_1$, $e_1$, $f_1$, $d_2$, $e_2$, $f_2$ are stored.

According to a second embodiment, said values of said parameters a, b, c, $q_1$, $q_2$, $d_1$, $e_1$, $f_1$, $d_2$, $e_2$, $f_2$ are entered into the apparatus via said input.

As regards the determination of said values of said parameters a, b, c, $q_1$, $q_2$, $d_1$, $e_1$, $f_1$, $d_2$, $e_2$, $f_2$ and the characteristics of the dynamic parameter P, deformation $q_w$ and temperature $T_w$, reference should be made to that already stated further above.

BRIEF DESCRIPTION OF THE DRAWINGS

The accompanying drawings, which are incorporated in and constitute a part of the specification, illustrate several embodiments of the invention, and, together with the general description given above and the detailed description of the embodiments given below, serve to explain the principles of the invention.

In the drawings.

DETAILED DESCRIPTION OF THE PREFERRED EMBODIMENTS

Figure 1:
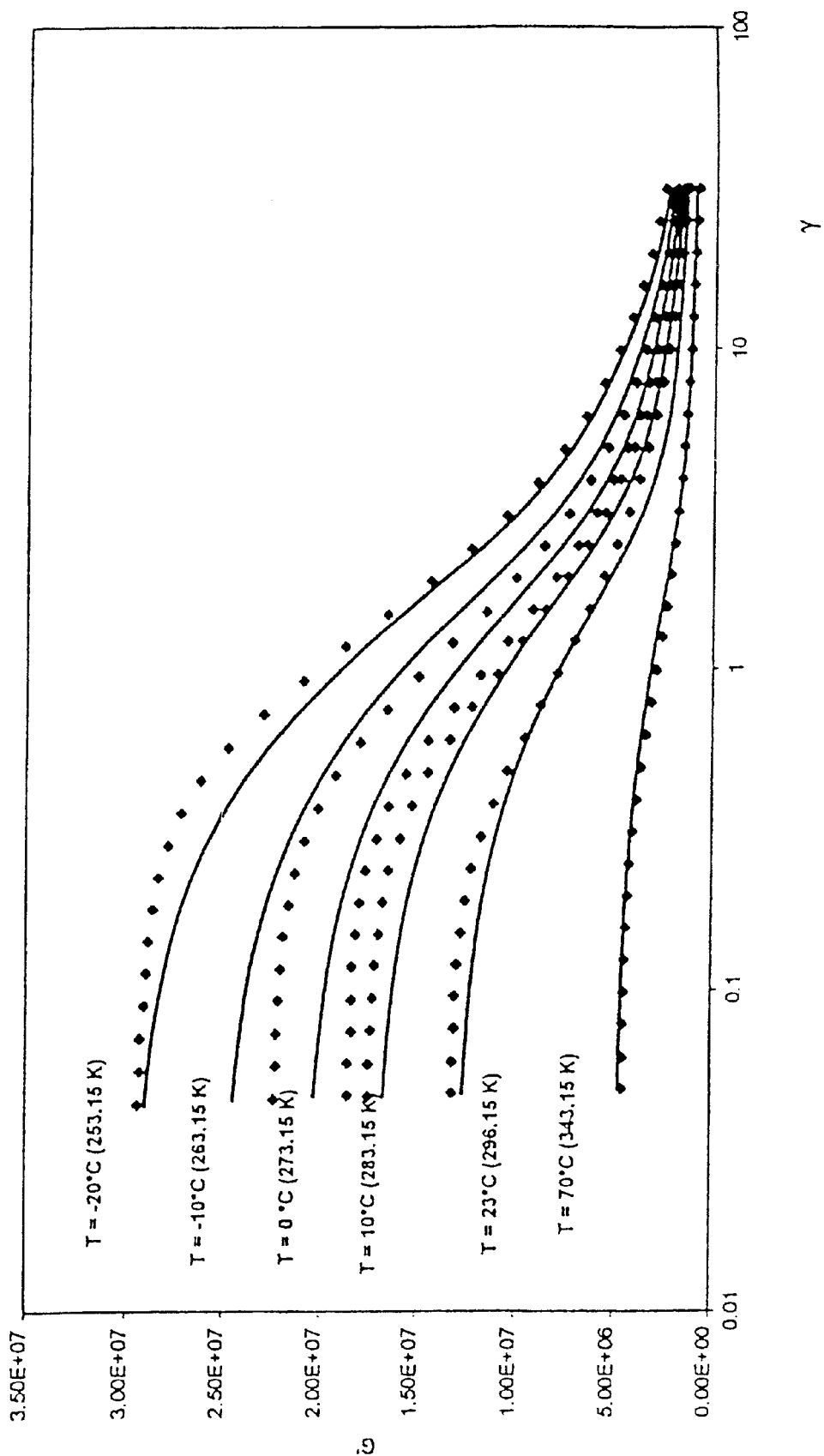
FIG. 1 shows elastic modulus as a function of deformation.

According to the present invention, in order to characterize a dynamic property P as a function of a deformation q of a viscoelastic material at a temperature $T_w$ at which no experimental measurement has been performed, the results of at least 5 experimental measurements, carried out at each of at least three temperatures $T_x$, $T_y$, $T_z$, of said dynamic parameter P as a function of said deformation q are sufficient. In fact, on the basis of these experimental measurements, it is possible to determine values of the abovementioned parameters a, b, c, $q_1$, $q_2$, $d_1$, $e_1$, $f_1$, $d_2$, $e_2$, $f_2$, on the basis of which, inserted in the relation (A), it is possible to obtain the progression of the dynamic parameter P as a function of the deformation q also at the temperature $T_w$, different from $T_x$, $T_y$, and $T_z$, at which experimental measurements have not been performed.

The present invention therefore has the advantage of reducing the number of experimental measurements which must be performed in order to characterize a viscoelastic material.

Moreover, as a result of the present invention, it is possible to select, from among a plurality of viscoelastic materials, that material/those materials for which a preselected dynamic parameter P best approximates a desired value $P_w$ for a preselected deformation $q_w$ at a temperature $T_w$ at which experimental measurements have not been performed. Namely, with the present invention it is possible to define a product having the required characteristics even though experimental measurements at the temperature concerned have not been performed at the moment in which said defining operation is performed.

Obviously, instead of defining a single product having a predetermined value $P_w$ of said predetermined dynamic parameter P, with the invention it is also possible to define classes of materials for which, at a preselected deformation $q_w$ and temperature $T_w$, a dynamic parameter P is greater or less than a given threshold value $P_w$.

The invention therefore simplifies, at the time of use, the process for selection of the viscoelastic material (or viscoelastic materials) which, from among those characterized, best satisfies (or satisfy) the final dynamic requirements of a desired product.

Finally, with the present invention it is possible to improve storage of N measured experimental values of a dynamic parameter P as a function of a deformation q at each of M temperatures T, reducing the number of values to be stored from (2×N×M)+(M) to 11 (in addition to the experimentally measured values of a dynamic parameter P it is also necessary to store the corresponding deformation values N and temperature values M used in the measurement). Since, in order to characterize univocally the dynamic properties of a viscoelastic material, it is necessary to know the behaviour of at least two dynamic parameters as a function of the deformation and the temperature (for example, the elastic modulus P' and the viscous modulus P") and since, for each dynamic parameter, many measurements (N≧5, M≧3) are generally necessary, it is obvious that with the method according to the invention it is possible to reduce considerably the number of values to be stored.

EXAMPLE 1

60 parts by weight of carbon black, type N234, and vulcanizing agents, vulcanization accelerators, activating agents, anti-ageing agents and conventional plasticizers well known in the manufacture of compounds for treads were added to 100 parts by weight of a compound for tyre treads consisting of a mixture of 70 parts by weight of Styrene Butadiene Rubber (SBR), 20 parts by weight of Butadiene Rubber (BR) and 10 parts by weight of natural rubber (NR). The compound thus obtained was then subjected to a conventional vulcanization treatment based on sulphur at a temperature of 151° C. for 30 minutes. Finally, cylindrical test pieces with a diameter of 5±0.2 mm and height of 6±0.2 mm were prepared from this compound.

Torsional tests at a frequency of 1 Hz and at temperatures of (−20, −10, 0, 10, 23, 70)±2° C. for different values of the torsional angle α applied were carried out on these test pieces. For this purpose a machine known as an Asphalt Analyser made by the company RHEOMETRIC was used, said machine having been set up beforehand for analysing the behaviour of the test piece in a range of deformations comprised between 0.05% and 40%, with logarithm-type scanning of the deformations applied.

With this arrangement, considering that the dependency of the deformation γ of the applied torsional angle α is expressed by the following relation:

$$\gamma(\%) = \alpha \times \frac{R}{h} \times 100$$

where

R and h are the radius and the height of the cylindrical test piece, respectively, the machine provided 29 measured values of the elastic modulus G'—expressed in Pascal (Pa)—as a function of 29 values of the deformation γ—expressed in %—for each of the 6 temperature values considered.

These values for the deformation γ, elastic modulus G' and temperature were used, according to the invention, to determine, for subsequent approximations, values of the parameters a, b, c, $q_1$, $q_2$, $d_1$, $e_1$, $f_1$, $d_2$, $e_2$, $f_2$.

Figure 5:
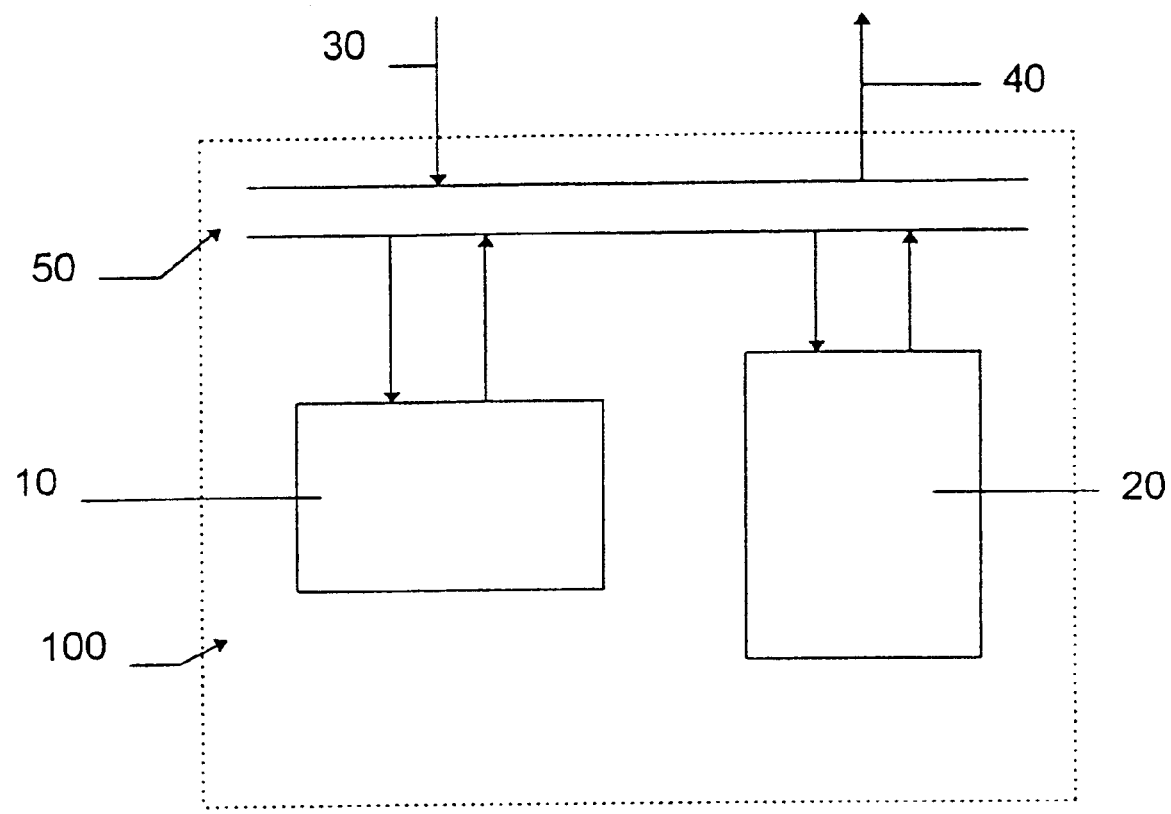
FIG. 5 is a block diagram of an apparatus according to one embodiment of the present invention.

More particularly, these values of the parameters a, b, c, $q_1$, $q_2$, $d_1$, $e_1$, $f_1$, $d_2$, $e_2$, $f_2$ were determined with an apparatus 100 which, according to the invention, comprises (FIG. 5) an input 30, a processing unit 10, a memory 20, an output 40 and connection lines 50.

Via said input 30, said 29 experimentally determined values of said elastic modulus G' as a function of said 29 values of the deformation γ at said six temperatures (−20, −10, 0, 10, 23, 70)±2° C. were entered. Said processing unit 10 was then activated by a suitable calculator programme so as to:

1) assign an arbitrary value for each of the parameters a, b, c, $q_1$, $q_2$, $d_1$, $e_1$, $f_1$, $d_2$, $e_2$, $f_2$;
2) insert this arbitrary value of the parameters a, b, c, $q_1$, $q_2$, $d_1$, $e_1$, $f_1$, $d_2$, $e_2$, $f_2$, in the abovementioned relation (A);
3) use said relation (A), in which said arbitrary values were inserted, in order to calculate, at each of said six temperatures (−20, −10, 0, 10, 23, 70)±2° C., twenty-nine values of G' as a function of the abovementioned twenty-nine values of γ used in the experimental measurements;
4) calculate the differences between the values of G' thus calculated and the corresponding values measured experimentally;
5) add together the squares of the abovementioned differences; and
6) on the basis of the result obtained, assign another value to each of the parameters a, b, c, $q_1$, $q_2$, $d_1$, $e_1$, $f_1$, $d_2$, $e_2$, $f_2$, so as to reduce the sum of the squares of the abovementioned differences.

Said processing unit 10 then repeated the abovementioned steps 2) to 6) until said sum of the squares of the differences was minimized and values of the parameters a, b, c, $q_1$, $q_2$, $d_1$, $e_1$, $f_1$, $d_2$, $e_2$, $f_2$ were thus obtained, said values, inserted in the relation (A), generating values of G' which best approximated those obtained experimentally.

The values of the parameters a, b, c, $q_1$, $q_2$, $d_1$, $e_1$, $f_1$, $d_2$, $e_2$, $f_2$ thus determined were then stored in the memory 20 and output (displayed on a computer screen) via the output 40.

These values are shown as follows:

a=9.71E+01;
b=−1.85E+04;
c=1.88E+06;
$d_1$=8.39E+02;
$e_1$=−2.24E+05;
$f_1$=1.48E+07;
$q_1$=1.45E+00;
$d_2$=1.43E+03;
$e_2$=−1.51E+05;
$f_2$=4.20E+06;
$q_2$=8.38E+00.

These values were then inserted by said processing unit in the abovementioned relation (A) in order to determine the progression of G' as a function of the torsion γ at the temperatures of (−20, −10, 0, 10, 23, 70)±2° C.

The progressions of G' as a function of the torsion γ thus determined were then stored in the memory 20 and output (displayed on a computer screen) via the output 40.

FIG. 1 shows the curves which represent the progression of G' (expressed in Pascal) as a function of γ (expressed in %), obtained with the method according to the invention (solid lines) and the corresponding experimental curves which pass through all the points (shown as squares) which represent the values of G' determined experimentally.

As it can be seen, the mean error of the elastic modulus G' calculated using the method according to the invention is equal to about 3% of the mean value measured. In other words, the curve obtained by means of the method according to the invention has a mean deviation, from the curve obtained using the experimental values, of about 3%.

By using the relation (A) and determining a suitable value for each of the parameters a, b, c, $q_1$, $q_2$, $d_1$, $e_1$, $f_1$, $d_2$, $e_2$, $f_2$, the method according to the invention therefore enables one to reproduce accurately the results obtained experimentally.

Moreover, it should be noted that the experimental curves according to FIG. 1 are the result of 29×6 values of elastic modulus G' measured as a function of 29 values of the deformation at 6 different temperatures, equal to (N×M)+(N+M)=(29*6)+(29+6)=209 values to be stored. As a result of the invention, therefore, it is possible to reduce the values to be stored for characterization of a dynamic property of a viscoelastic material, from 209 to 11, i.e. to about 5.3% of the initial value.

Even though, in this example, at the 6 temperatures of (−20, −10, 0, 10, 23, 70)±2° C. the same values for the deformation γ were used, the person skilled in the art will nevertheless easily realize that deformation values which are different from one temperature to another may be used without thereby altering the spirit of the present invention.

EXAMPLE 2

The same procedure as that used in the preceding Example 1 was used, except that 30 phr (parts by weight per 100 parts of polymeric matrix) of carbon black, type N234, and 30 phr of silica, type VN3, distributed by DEGUSSA and with a surface area equal to 160 m²/g were added to the polymeric composition.

The torsional tests were carried out at the temperatures of (−10, 23, 70)±2° C.

Application of the method according to the invention, as already described above, produced values of the parameters a, b, c, $q_1$, $q_2$, $d_1$, $e_1$, $f_1$, $d_2$, $e_2$, $f_2$ which generate three curves which best approximate the three experimental curves passing through all the points determined experimentally at said temperatures of (−10, 23, 70)±2° C.

The abovementioned values of the parameters a, b, c, $q_1$, $q_2$, $d_1$, $e_1$, $f_1$, $d_2$, $e_2$, $f_2$ were then inserted in the abovementioned relation (A) in order to determine the progression of the elastic modulus G' as a function of the deformation γ at the temperatures of 0° C. and 10° C. at which experimental measurements had not yet been performed.

Subsequently, by way of comparison, experimental measurements of the elastic modulus G' as a function of the deformation γ also at the temperatures of 0° C. and 10° C. were performed.

FIG. 2 shows:

the curves which pass through all the points (shown as squares) which represent the values of G' (expressed in Pascal) as a function of γ (expressed in %) determined experimentally at the temperatures of −10, 23 and 70° C.;

the curves representing the progression of G' as a function of γ, obtained by means of the method according to the invention at the temperatures of −10, 23 and 70° C. (solid lines);

the curves representing the progression of G' as a function of γ, obtained by means of the method according to the invention at the temperatures of 0 and 10° C. (solid lines);

the curves which pass through all the points (shown as squares) which represent the values of G' as a function of γ, determined experimentally at the temperatures of 0 and 10° C.

Figure 2:
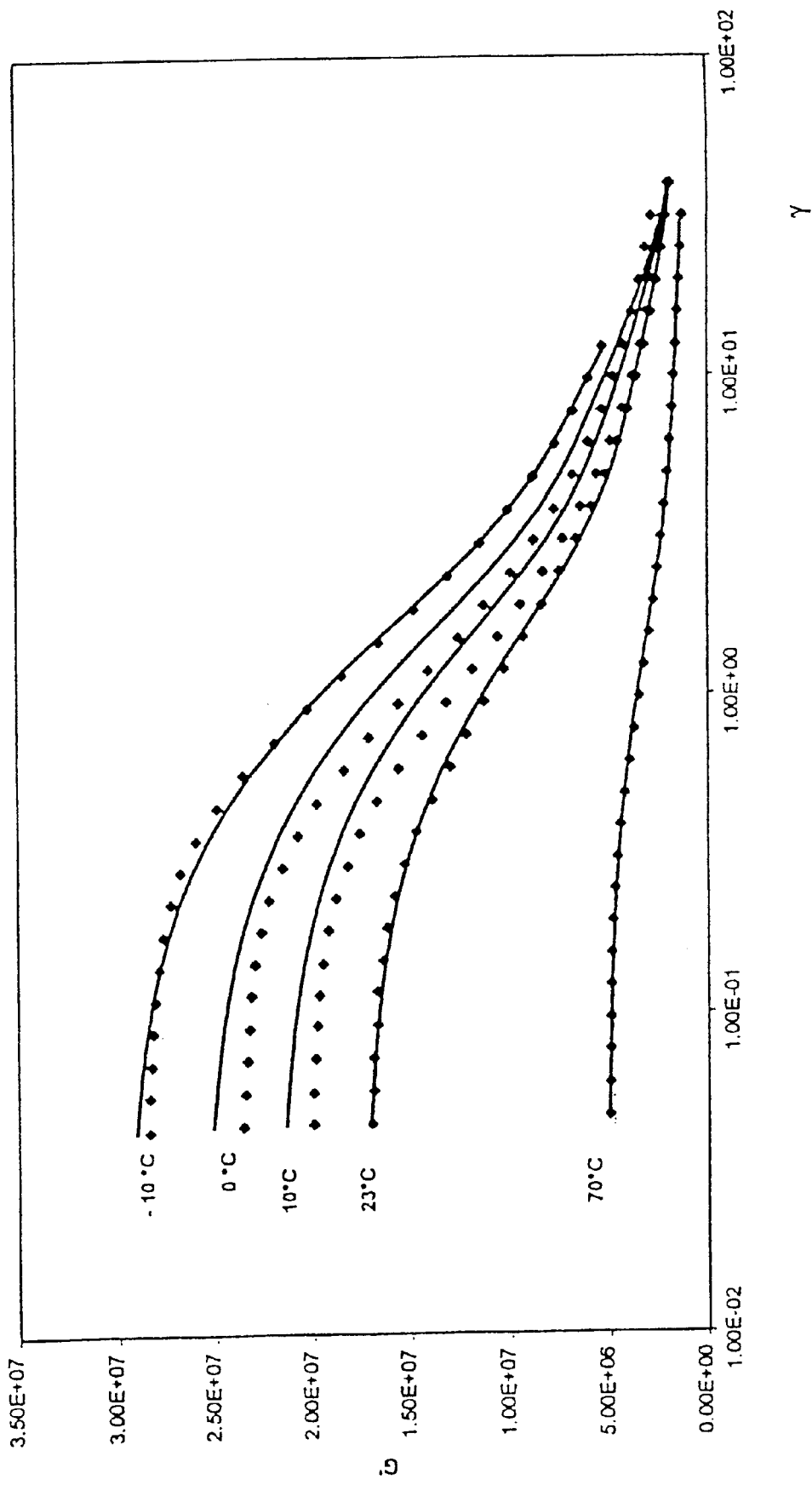
FIG. 2 also shows elastic modulus as a function of deformation.

FIG. 2 shows that even though the values of the parameters a, b, c, $q_1$, q2, $d_1$, $e_1$, $f_1$, $d_2$, $e_2$, $f_2$ were determined only on the basis of the experimental measurements performed at the temperatures of −10, 23 and 70° C., there is an excellent correlation between the experimental values and the values calculated by means of the relation (A) also in the case of the curves plotted at the temperatures of 0 and 10° C.

EXAMPLE 3

The same procedure as that used in the preceding Example 1 was used, except for the fact that the viscous modulus G" was measured.

By applying the method according to the invention as described above, the following values for the parameters a, b, c, $q_1$, $q_2$, $d_1$, $e_1$, $f_1$, $d_2$, $e_2$, $f_2$ were obtained:

a=292.38;
b=−28985.6;
c=860063.91;
$d_1$=−607.41;
$e_1$=75866.44;
$f_1$=−2677405.17;
$q_1$=0.7617;
$d_2$=686.74;
$e_2$=−94057.14;
$f_2$=4066687.48;
$q_2$=5.272.

These values were then inserted in the abovementioned relation (A) in order to determine the progression of G" as a function of the torsion γ at the temperatures of (−20, −10, 0, 10, 23, 70)±20° C.

Figure 3:
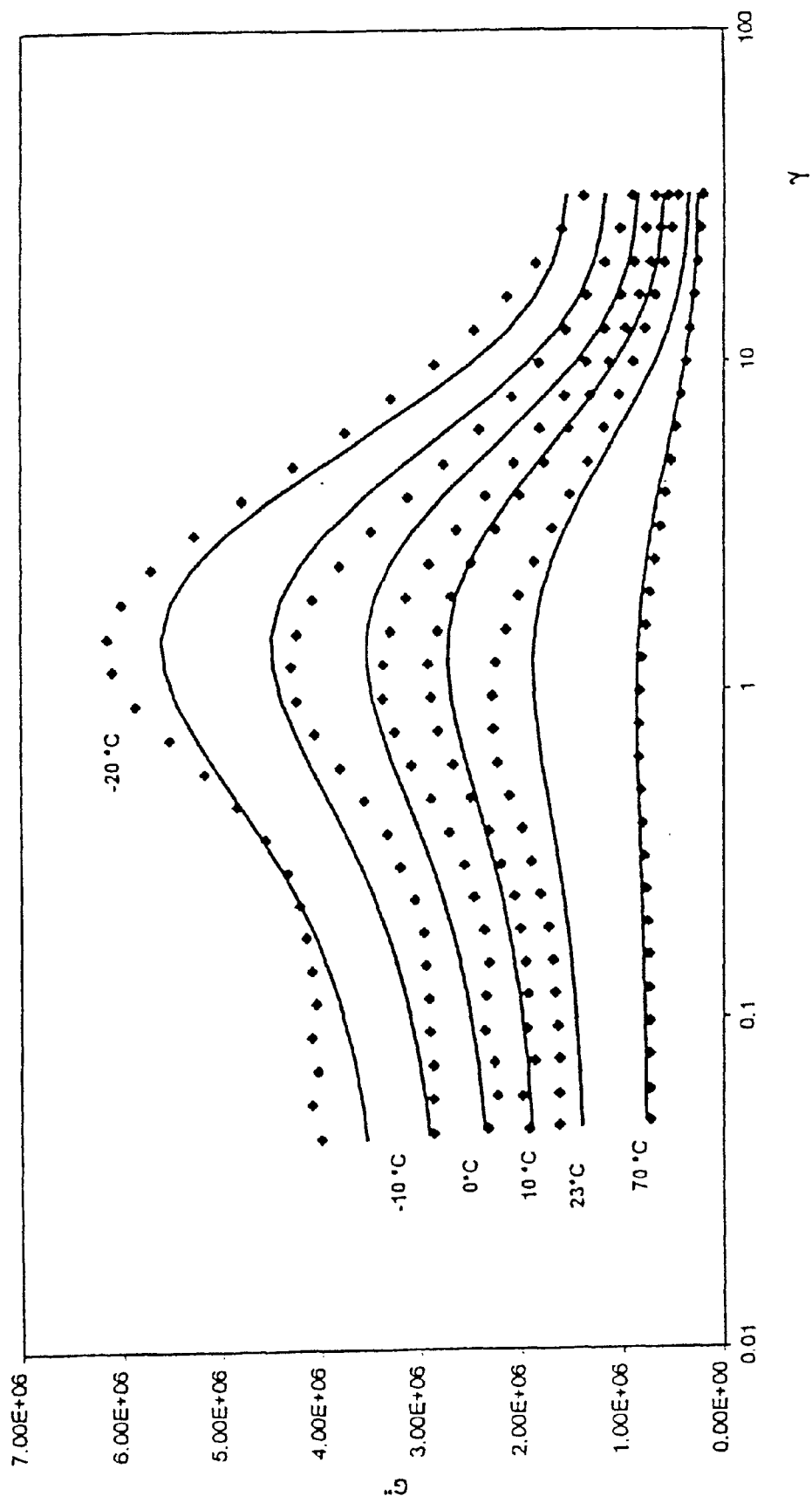
FIG. 3 shows viscous modulus as a function of deformation.

FIG. 3 shows the curves thus obtained (solid lines) which represent the progression of G" (expressed in Pascal) as a function of γ (expressed in %) and the corresponding experimental curves which pass through all the points (shown as squares) which represent the values determined experimentally.

In this case also, it will be noted that there is an excellent correlation between the values obtained experimentally and those determined by means of the relation (A) in accordance with the method of the invention.

EXAMPLE 4

The same procedure as that used in the preceding Example 2 was used, except that the viscous modulus G' as a function of the deformation γ at the temperatures of −10, 23 and 70° C. was measured.

By applying the method according to the invention, the following values for the parameters a, b, c, $q_1$, $q_2$, $d_1$, $e_1$, $f_1$, $d_2$, $e_2$, $f_2$ were obtained:

a=415.14;
b=−48116.2;
c=1613000.35;
$d_1$=−584.28;
$e_1$=77979.45;
$f_1$=−2768211.79;
$q_1$=0.7136;
$d_2$=593.61;
$e_2$=−94259.56;
$f_2$=4403028.61;
$q_2$=5.327.

The abovementioned values of the parameters a, b, c, $q_1$, $q_2$, $d_1$, $e_1$, $f_1$, $d_2$, $e_2$, $f_2$ were then inserted in the abovementioned relation (A) so as to plot the curves for the progression of the viscous modulus G" as a function of the deformation γ at the temperatures of 0° C. and 10° C. at which experimental measurements had not yet been performed.

Subsequently, by way of comparison, experimental measurements of the viscous modulus G" as a function of the deformation γ were also performed at the temperatures of 0° C. and 10° C.

Figure 4:
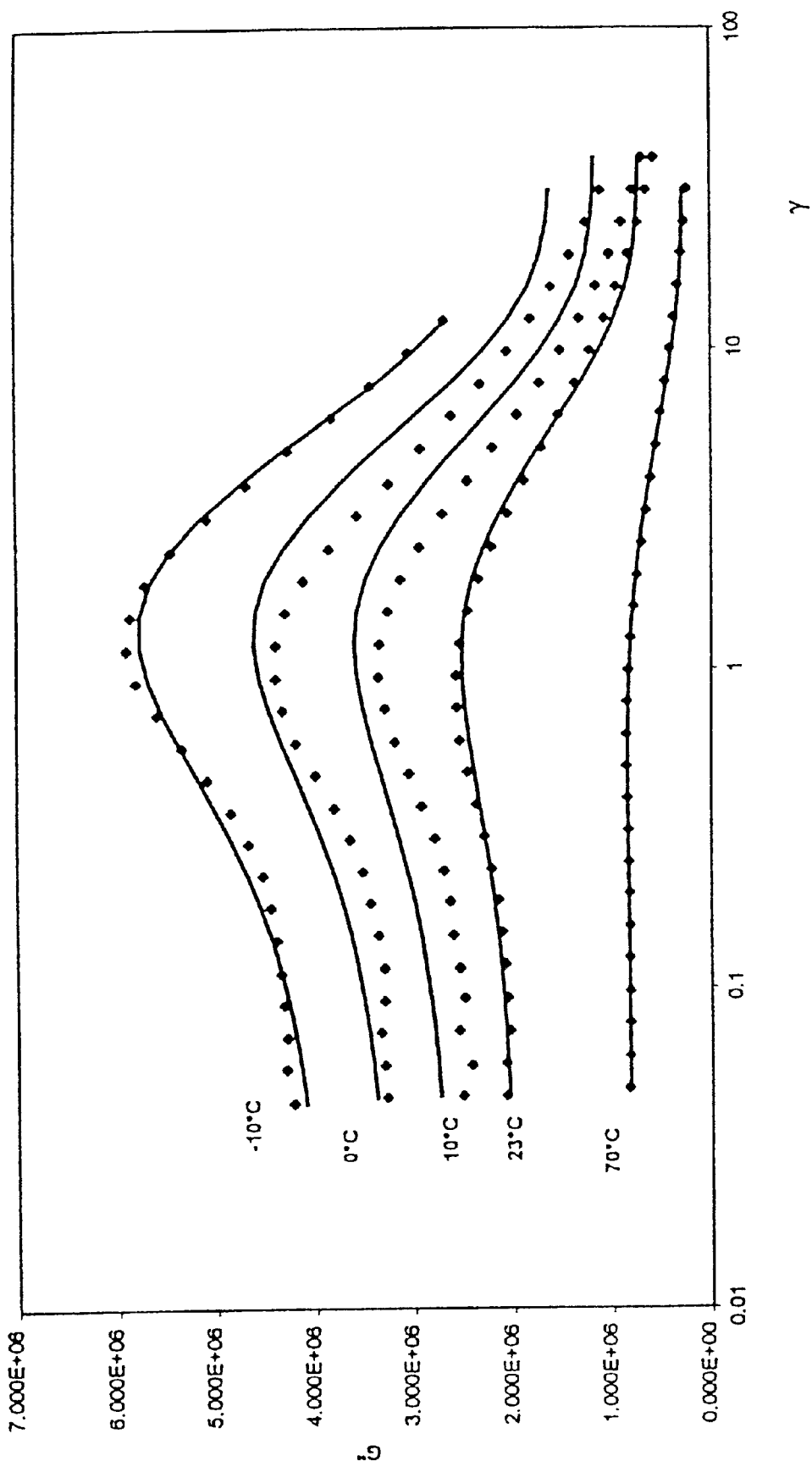
FIG. 4 also shows viscous modulus as a function of deformation.

FIG. 4 shows
the curves which pass through all the points (represented by squares) which represent the values of G" (expressed in Pascal) as a function of γ (expressed in %) determined experimentally at the temperatures of −10, 23 and 70° C.;
the curves representing the progression of G" as a function of γ, obtained by means of the methods according to the invention at the temperatures of −10, 23 and 70° C. (solid lines);
the curves representing the progression of G" as a function of γ, obtained by means of the methods according to the invention at the temperatures of 0 and 10° C. (solid lines);
the curves which pass through all the points (shown as squares) which represent the values of G" as a function of γ, determined experimentally at the temperatures of 0 and 10° C.

In this case also, FIG. 4 shows that despite the fact that the values of the parameters a, b, c, $q_1$, $q_2$, $d_1$, $e_1$, $f_1$, $d_2$, $e_2$, $f_2$ were determined only on the basis of the experimental measurements performed at the temperatures of −10, 23 and 70° C., there is an excellent correlation between experimental values and values calculated by means of the relation (A) also in the case of the curves plotted at the temperatures of 0 and 10° C.

As can be seen from Examples 1 to 4, with the method according to the invention it is possible to reproduce the experimentally measured values of a dynamic parameter P. The minimum deviations which arise between the experimental curves and those determined using the abovementioned relation (A) do not alter at all the reliability of the calculations performed subsequently, on the basis of the calculated values of P', P", P* and tan δ as a function of q, during design of products such as, for example, motor vehicle tyres.

From the above examples it is also obvious that, with the method according to the invention, it is possible to determine the progression of a dynamic parameter P as a function of a deformation q at a temperature $T_w$ at which experimental measurements have not been performed and reduce considerably the number of values which must be stored in order to retain a series of experimental measurements carried out on a viscoelastic material.

What is claimed is:

1. A method for determining behavior of a viscoelastic material at a first temperature, comprising:
performing five or more measurements of a dynamic parameter as a function of deformation at each of at least a second, third, and fourth temperature;
choosing from the measurements eleven or more data points, wherein each data point comprises a value of the dynamic parameter, an associated deformation, and an associated temperature;
determining values of parameters a, b, c, $q_1$, $q_2$, $d_1$, $e_1$, $f_1$, $d_2$, $e_2$, and $f_2$ by inserting at least eleven of the data points into a first equation $$P(q, T) = a*T^2 + b*T + c + (d_1*T^2 + e_1*T + f_1)*e^{-\frac{q}{q_1}} + (d_2*T^2 + e_2*T + f_2)*e^{-\frac{q}{q_2}}$$

in which P represents the value of a respective dynamic parameter, q represents the associated deformation, and T represents the associated temperature;

inserting the first temperature and the values of the parameters a, b, c, $q_1$, $q_2$, $d_1$, $e_1$, $f_1$, $d_2$, $e_2$, and $f_2$ into the first equation; and approximating the dynamic parameter as a function of the deformation at the first temperature using the first equation.

2. The method of claim 1, further comprising, for one or more of the at least a second, third, and fourth temperatures, approximating the measurements of the dynamic parameter as a function of the deformation at a respective temperature.

3. The method of claim 1, further comprising, for one or more of the at least a second, third, and fourth temperatures, plotting a curve approximating the measurements of the dynamic parameter as a function of the deformation at a respective temperature.

4. The method of claim 1, wherein the dynamic parameter comprises:
an elastic modulus of the viscoelastic material; or
a viscous modulus of the viscoelastic material; or
a complex modulus of the viscoelastic material; or
a loss factor of the viscoelastic material.

5. The method of claim 1, wherein, in the choosing step, at least two values of the dynamic parameter and the associated deformation are chosen for each of the at least a second, third, and fourth temperature.

6. The method of claim 1, wherein, when greater accuracy is desired, additional required parameters are determined and, in place of the first equation, a second summation equation (I) is used $$P(q,T) = a*T^2 + b*T + c + \sum_{i=1}^{\infty}(d_i*T^2 + e_i*T + f_i)*e^{-\frac{q}{q_i}} \qquad (I)$$

wherein:
q represents the deformation expressed in %;
T represents the temperature expressed in degrees Kelvin;
a, b, and c represent characteristic constants depending on the viscoelastic material and the dynamic parameter;
$d_i$, $e_i$, and $f_i$ represent characteristic constants depending on an effect of the temperature on the dynamic parameter and on an ith characteristic deformation; and
$q_i$ represents a characteristic deformation at an ith exponential.

7. A method for improving storage of parameters related to behavior of a viscoelastic material, comprising:
performing five or more measurements of a dynamic parameter as a function of deformation at each of at least a second, third, and fourth temperature;
choosing from the measurements eleven or more data points, wherein each data point comprises a value of the dynamic parameter, an associated deformation, and an associated temperature;
determining values of parameters a, b, c, $q_1$, $q_2$, $d_1$, $e_1$, $f_1$, $d_2$, $e_2$, and $f_2$ by inserting at least eleven of the data points into a first equation $$P(q,T) = a*T^2 + b*T + c +$$
$$(d_1*T^2 + e_1*T + f_1)*e^{-\frac{q}{q_1}} + (d_2*T^2 + e_2*T + f_2)*e^{-\frac{q}{q_2}}$$

in which P represents the value of a respective dynamic parameter, q represents the associated deformation, and T represents the associated temperature;
storing the values of the parameters a, b, c, $q_1$, $q_2$, $d_1$, $e_1$, $f_1$, $d_2$, $e_2$, and $f_2$.

8. The method of claim 7, wherein, when greater accuracy is desired, additional required parameters are determined and, in place of the first equation, a second summation equation (I) is used $$P(q,T) = a*T^2 + b*T + c + \sum_{i=1}^{\infty}(d_i*T^2 + e_i*T + f_i)*e^{-\frac{q}{q_i}} \qquad (I)$$

wherein
q represents the deformation expressed in %;
T represents the temperature expressed in degrees Kelvin;
a, b, and c represent characteristic constants depending on the viscoelastic material and the dynamic parameter;
$d_i$, $e_i$, and $f_i$ represent characteristic constants depending on an effect of the temperature on the dynamic parameter and on an ith characteristic deformation; and
$q_i$ represents a characteristic deformation at an ith exponential.

9. A method for identifying, from among a plurality of viscoelastic materials, at least one viscoelastic material having a dynamic parameter which, at a preselected temperature and deformation, satisfies a test versus a predetermined value, comprising:
determining, for each of the viscoelastic materials, a value of the dynamic parameter at the preselected temperature and deformation using a first equation $$P(q_w, T_w) = a*T_w^2 + b*T_w + c +$$
$$(d_1*T_w^2 + e_1*T_w + f_1)*e^{-\frac{q_w}{q_1}} + (d_2*T_w^2 + e_2*T_w + f_2)*e^{-\frac{q_w}{q_2}}$$

in which P represents the value of a respective dynamic parameter, $q_w$ represents the preselected deformation, and $T_w$ represents the preselected temperature, and
wherein, for each of the viscoelastic materials, values of parameters a, b, c, $q_1$, $q_2$, $d_1$, $e_1$, $f_1$, $d_2$, $e_2$, and $f_2$ have previously been determined;
comparing, for each of the viscoelastic materials, the value of the respective dynamic parameter with the predetermined value; and
selecting the viscoelastic materials for which, at the preselected temperature and deformation, the respective dynamic parameter satisfies the test.

10. The method of claim 9, wherein, when greater accuracy is desired, additional required parameters are determined and, in place of the first equation, a second summation equation (I) is used $$P(q,T) = a*T^2 + b*T + c + \sum_{i=1}^{\infty}(d_i*T^2 + e_i*T + f_i)*e^{-\frac{q}{q_i}} \qquad (I)$$

wherein:
q represents the deformation expressed in %;
T represents the temperature expressed in degrees Kelvin; and
necessary values of the parameters a, b, c, $d_i$, $e_i$, $f_i$, and $q_i$ have previously been determined.

11. An apparatus for processing data relating to a viscoelastic material having a predetermined dynamic parameter, the apparatus comprising:
an input;
a processing unit connected, directly or indirectly, to the input; and
a memory connected, directly or indirectly, to the processing unit;

wherein five or more measurements of a dynamic parameter as a function of deformation at each of at least a second, third, and fourth temperature are entered via the input, wherein the processing unit chosses from the measurements eleven or more data points, wherein each data point comprises a value of the dynamic parameter, an associated deformation, and an associated temperature, wherein the processing unit determines values of parameters a, b, c, $q_1$, $q_2$, $d_1$, $e_1$, $f_1$, $d_2$, $e_2$, and $f_2$ by inserting at least eleven of the data points into a first equation $$P(q, T) = a*T^2 + b*T + c + (d_1*T^2 + e_1*T + f_1)*e^{-\frac{q}{q_1}} + (d_2*T^2 + e_2*T + f_2)*e^{-\frac{q}{q_2}}$$

in which P represents the value of a respective dynamic parameter, q represents the associated deformation, and T represents the associated temperature, and wherein the memory stores the values of the parameters a, b, c, $q_1$, $q_2$, $d_1$, $e_1$, $f_1$, $d_2$, $e_2$, and $f_2$.

12. The apparatus of claim 11, wherein, for one or more of the at least a second, third, and fourth temperatures, the processing unit approximates the measurements of the dynamic parameter as a function of the deformation at a respective temperature.

13. The apparatus of claim 11, further comprising a unit for plotting curves;
wherein, for one or more of the at least a second, third, and fourth temperatures, the unit for plotting curves plots a curve approximating the measurements of the dynamic parameter as a function of the deformation at a respective temperature.

14. The apparatus of claim 11, wherein a first temperature is entered via the input,
wherein the processing unit inserts the values of parameters a, b, c, $q_1$, $q_2$, $d_1$, $e_1$, $f_1$, $d_2$, $e_2$, and $f_2$ into the first equation, and
wherein the processing unit approximates the dynamic parameter as a function of the deformation at the first temperature using the first equation.

15. The apparatus of claim 14, further comprising an output;
wherein the output provides the approximation from the apparatus.

16. The apparatus of claim 11, wherein, when greater accuracy is desired, additional required parameters are determined and, in place of the first equation, a second summation equation (I) is used $$P(q, T) = a*T^2 + b*T + c + \sum_{i=1}^{\infty} (d_i*T^2 + e_i*T + f_i)*e^{-\frac{q}{q_i}} \quad (I)$$

wherein:
q represents the deformation expressed in %;
T represents the temperature expressed in degrees Kelvin;
a, b, and c represent characteristic constants depending on the viscoelastic material and the dynamic parameter;

$d_i$, $e_i$, and $f_i$ represent characteristic constants depending on an effect of the temperature on the dynamic parameter and on an ith characteristic deformation; and
$q_i$ represents a characteristic deformation at an ith exponential.

17. An apparatus for processing data relating to a plurality of viscoelastic materials having a dynamic parameter, the apparatus comprising:
an input;
a processing unit connected, directly or indirectly, to the input; and
an output connected, directly or indirectly, to the processing unit;
wherein a predetermined value for the dynamic parameter at a preselected temperature and deformation is entered via the input,
wherein the processing unit determines, for each of the viscoelastic materials, a value of the dynamic parameter at the preselected temperature and deformation using a first equation $$P(q_w, T_w) = a*T_w^2 + b*T_w + c + (d_1*T_w^2 + e_1*T_w + f_1)*e^{-\frac{q_w}{q_1}} + (d_2*T_w^2 + e_2*T_w + f_2)*e^{-\frac{q_w}{q_2}}$$

in which P represents the value of a respective dynamic parameter, $q_w$ represents the preselected deformation, and $T_w$ represents the preselected temperature, and
wherein, for each of the viscoelastic materials, values of parameters a, b, c, $q_1$, $q_2$, $d_1$, $e_1$, $f_1$, $d_2$, $e_2$, and $f_2$ have previously been determined,
wherein the processing unit compares, for each of the viscoelastic materials, the value of the respective dynamic parameter with the predetermined value,
wherein the processing unit selects any viscoelastic materials for which, at the preselected temperature and deformation, the respective dynamic parameter satisfies a test versus the predetermined value, and
wherein the output provides the selections from the apparatus.

18. The apparatus of claim 17, wherein, when greater accuracy is desired, additional required parameters are determined and, in place of the first equation, a second summation equation (I) is used $$P(q, T) = a*T^2 + b*T + c + \sum_{i=1}^{\infty} (d_i*T^2 + e_i*T + f_i)*e^{-\frac{q}{q_i}} \quad (I)$$

wherein:
q represents the deformation expressed in %;
T represents the temperature expressed in degrees Kelvin; and
necessary values of the parameters a, b, c, $d_i$, $e_i$, $f_i$, and $q_i$ have previously been determined.

* * * * *